United States Patent [19]

Scheinman et al.

[11] Patent Number: 5,429,131
[45] Date of Patent: Jul. 4, 1995

[54] MAGNETIZED ELECTRODE TIP CATHETER

[75] Inventors: Melvin M. Scheinman, San Francisco; Thomas F. Kordis, Sunnyvale, both of Calif.

[73] Assignee: The Regents of the University of California, Oakland, Calif.

[21] Appl. No.: 201,973

[22] Filed: Feb. 25, 1994

[51] Int. Cl.⁶ .......................... A61B 5/04; A61N 1/05
[52] U.S. Cl. .................................. 128/642; 128/696; 606/41; 607/122
[58] Field of Search ............... 128/642, 695, 657, 656, 128/658, 696, 702, 705; 606/124, 47, 33, 41, ; 607/122, 125

[56] References Cited

U.S. PATENT DOCUMENTS

| | | | |
|---|---|---|---|
| 3,794,041 | 2/1974 | Frei et al. | 128/348 |
| 3,961,632 | 6/1976 | Moossun | 128/347 |
| 3,986,493 | 10/1976 | Hendren, III | 128/1.3 |
| 4,004,298 | 1/1977 | Freed | 3/1 |
| 4,077,412 | 3/1978 | Moossun | 128/347 |
| 4,162,679 | 7/1979 | Reenstierna | 128/419 P |
| 4,619,247 | 10/1986 | Inoue et al. | 128/6 |
| 4,641,649 | 2/1987 | Walinsky et al. | 128/303.1 |
| 4,809,713 | 3/1989 | Grayzel | 128/785 |
| 4,832,048 | 5/1989 | Cohen | 127/786 |
| 4,940,064 | 7/1990 | Desai | 128/784 |
| 4,945,912 | 8/1990 | Langberg | 128/642 |
| 5,056,517 | 10/1991 | Fenici | 128/419 |
| 5,125,888 | 6/1992 | Howard et al. | 600/12 |

OTHER PUBLICATIONS

Scheinman, M. M., and Davis, M. D., "Catheter ablation for treatment of tachyarrhythmias: present role and potential promise," *Circulation*, 73(1):10–13 (Jan. 1986).
Scheinman, M. M., "Ablation therapy for patients with supraventicular tachycardia," *Ann. Rev. Med.*, 37:225–233 (1986).
Wetstein, L., et al., "Propensity to develop ventricular tachyarrhtyhmias: differences in homgeneous versus heterogeneous myocardial infarcts," *Puerto Rico Health Sciences Journal*, 4(2):79–89 (Jun. 1985).
Kutcher, K. L., "Cardiac Electrophysiologic Mapping Techniques," *Focus on Critical Care*, 12(4):26–30 (Aug. 1985).
Scheinman, M. M., "Catheter abalation of the atrioventicular junction: a report of the percutaneous mapping and ablation registry," *Circulation*, 70(6):1024–1029 (Dec. 1984).
Hartzler, G. O., "Electrode Catheter Ablation of Refractory Focal Ventricular Tachycardia," *JACC*, 2(6):1107–13 (Dec. 1983).
Josephson, M. E., "Recurrent Sustained Ventricular Tachycardia: 2. Endocardial Mapping," *Circulation*, 57(3):440–447 (Mar. 1978).
Scheinman, M. M., "Emerging Technologies in Antiarrhythmic Therapy," 24 pp. (publisher and date unknown).
Fackelmann, K. A., "Cardiac Electricians—Radio waves can cure a racing heart," 2 pp. (publisher and date unknown).

*Primary Examiner*—Lee S. Cohen
*Assistant Examiner*—Stephen Huang
*Attorney, Agent, or Firm*—Townsend and Townsend Khourie and Crew

[57] ABSTRACT

Tachycardial arrhythmias are located and ablated by a combination of first and second catheters which are mutually attracted by magnetized regions at their distal ends. One of the catheters contains mapping electrodes and is initially used to ascertain the locus of the arrhythmia by conventional mapping. Once this is accomplished, the catheter is allowed to remain in position while the second catheter is inserted in such a manner that mutual magnetic attraction between the two occurs across cardiac tissue. One or the other of the two catheters also contains an ablation component at its tip, such that when the two catheter tips are held in position by virtue of their mutual magnetic attraction, ablation can be performed.

13 Claims, 3 Drawing Sheets

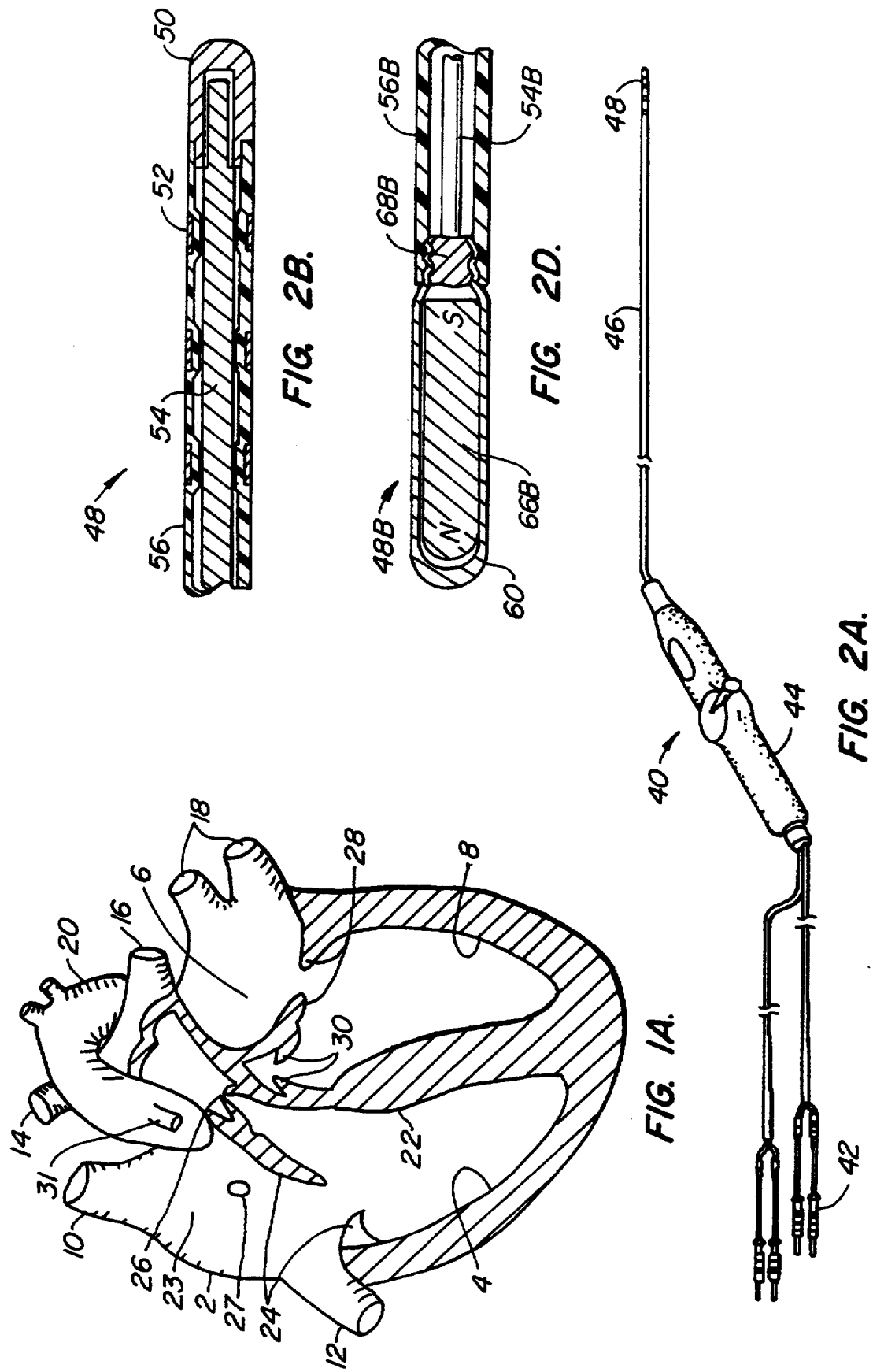

MAGNETIZED ELECTRODE TIP CATHETER

BACKGROUND OF THE INVENTION

Abnormal heart beats or cardiac arrhythmias can cause significant morbidity and mortality. These arrhythmias arise from a variety of causes, including atherosclerotic heart disease, ischemic heart disease, metabolic or hemodynamic derangements, rheumatic heart disease, cardiac valve disease, certain pulmonary disorders and congenital etiologies.

The normal heart rate is about 60 to 100 beats per minute. Arrhythmias, also called dysrhythmias, include tachycardias at rates exceeding 100 beats per minute for a duration of at least 3 beats. Tachycardias are also referred to as tachyarrhythmias. Sometimes no treatment is required, such as in the tachycardia following a physiologic response to stress or exercise. However, in some cases, treatment is required to alleviate symptoms or to prolong the patient's life.

A variety of treatments exists, including electric direct current cardioversion, pharmacologic therapy with drugs such as quinidine, digitalis, and lidocaine, treatment of an underlying disorder such as a metabolic derangement, and ablation by either percutaneous (closed chest) or surgical (open chest) procedures. Treatment by ablation involves destruction of a portion of cardiac tissue which displays an abnormal electrical function.

For clinical information concerning ablation therapy for supraventricular tachycardia, ventricular tachycardia and junctional ablation, see the following articles: Scheinman, Melvin M., "Ablation Therapy for Patients with Supraventricular Tachycardia," *Ann. Rev. Med.* 37:225-233 (1986); Hartzler, Geoffrey O., "Electrode Catheter Ablation of Refractory Focal Ventricular Tachycardia," *JACC* 2(6):1107-1113 (December 1983); Josephson, et al., "Recurrent Sustained Ventricular Tachycardia," *Circulation* 57(3):440-447 (March 1978); and Scheinman, et al., "Catheter Ablation of the Atrioventricular Junction: A Report of the Percutaneous Mapping and Ablation Registry," *Circulation* 70(6): 1024-1029 (December 1984).

Normally, the heart possesses an intrinsic pacemaker function in the sinoatrial (SA) node, which is in the right atrium, adjacent to the entrance of the superior vena cava. The right atrium is one of four proper anatomic chambers of the heart. The other chambers are the right ventricle, the left atrium, and the left ventricle. The superior vena cava is a major source of venous return to the heart.

The SA node possesses an area of specialized cardiac tissue called Purkinje cells which usually measures about 1½ centimeters by about 2½ millimeters. An electrical impulse normally exits from the SA node and travels across the atrium until it reaches the atrioventricular (AV) node. The AV node is located in the right atrium near the ventricle.

Emerging from the AV node is a specialized bundle of cardiac muscle cells which originates at the AV node in the interatrial septum. This "bundle of His" passes through the atrioventricular junction and later divides into left and right branches which supply the left and right ventricles. The left and right bundles further give rise to branches which become the so-called distal His-Purkinje system, which extends throughout both ventricles.

In a normal situation, therefore, an impulse originates intrinsically at the SA node, transmits through the atrium and is modified by the AV node. The AV node passes the modified impulse throughout the left and right ventricles via the His-Purkinje system to result in a coordinated heartbeat at a normal rate. Many factors affect the heart rate in addition to the intrinsic conduction system. For example, normally the heart rate will respond to physiologic parameters such as stress, exercise, oxygen tension and vagal influences.

Abnormal tachycardia, can arise from a number of causes. One group of such causes relates to abnormalities in the heart's conduction system. For instance, an ectopic or abnormally positioned electrical focus may take over the normal function of a node such as the SA or AV node. In addition to abnormal automaticity, arrhythmias may develop on the basis of accessory pathways bridging atrium with ventricle. Such pathways act as short circuits serving to maintain abnormal rhythms.

Treatment of abnormal tachycardias arising from ectopic foci or so-called ectopic pacemakers can include pharmacologic therapy or ablative therapy. The latter refers to destruction of the tissue responsible for the genesis and perpetuation of the arrhythmias. The ablative therapy may be accomplished by percutaneous insertion of a catheter or by surgical cardiac procedures.

Normally, when performing a percutaneous or closed chest cardiac ablation procedure, fluoroscopy is used to visualize the chambers of the heart. Fluoroscopy uses roentgen rays (X-rays) and includes use of a specialized screen which projects the shadows of the X-rays passing through the heart.

The technique of percutaneous ablation includes cardiac catheterization. A catheter is placed in an artery or a vein of the patient depending typically on whether the left (ventricle and/or atrium) or right (ventricle and/or atrium) side of the heart is to be explored and portions thereof ablated. For example, the left atrium can be entered by forcing the catheter through the interatrial septum after advancing the catheter from a vein and into the right atrium.

Frequently, an artery or vein in the groin, such as one of the femoral vessels, is selected for catheterization. The catheter is passed within the blood vessel and then into a vena cava or the aorta, depending whether a vein or an artery was entered, respectively, and from there into the appropriate atrium and/or ventricle. Vessels in addition to the femoral artery and/or vein can be used. Examples include the jugular, antecubital and subclavian vessels.

The catheter is steerable and it is positioned close to an endocardial or intravascular region of interest. "Endocardial" refers to the inner lining of the heart. An intravascular region can be of interest in part because the better approach anatomically to a cardiac electrical anomaly is sometimes by way of a vessel such as the coronary sinus.

The catheter includes electrodes as a means for sensing the electrical impulses originating in the heart. Thus, the electrode catheter can provide a number of readings from different areas of the internal aspects of the heart chambers proper and certain vessels, such as the coronary sinus, whose location provides an approach to the abnormally functioning cardiac tissue.

These various electrical recordings are correlated to provide an electrophysiologic map of the heart including notation of normal or abnormal features of the heart's conduction system. Once the electrophysiologic map is produced, an area can be selected for ablation.

For background information concerning catheter ablation and mapping techniques, see generally Scheinman, Melvin M. and Jesse C. Davis, "Catheter Ablation for Treatment of Tachyarrhythmias: Present Role and Potential Promise," *Circulation* 73(1): 10–13 (January 1986) and Kutcher, Karen L., "Cardiac Electrophysiologic Mapping Techniques," *Focus on Critical Care* 12(4):26–30 (August 1985).

Conventionally, a single catheter includes both mapping and ablation capabilities. For instance, an electrode catheter generally has four electrode tings positioned toward the distal end for mapping and a large electrode tip at the distalmost end of the catheter for RF ablation.

Steerable mapping and ablation catheters using RF energy are known. See, for example, U.S. Pat. No. 4,945,912 to Langberg. The RF energy is directed to the area to be ablated and causes tissue destruction by heat. RF ranges from $10^4$ Hertz (Hz) to $3 \times 10^{12}$ Hz. Generally RF as used herein refers to the range of from about 100 kilohertz (KHz) to about 1 million Hertz (MHz). Additionally, direct current electrical, laser or microwave energy or cryoablation can be used instead of RF energy. See, for example, U.S. Pat. No. 4,641,649 to Walinsky.

Alternatively, ethanol has been infused into coronary arteries to ablate a focus such as a ventricular arrhythmia focus or the AV node. Unfortunately, this tends to result in a fairly large region of cardiac tissue death or myocardial infarction. With transarterial infusion, there is difficulty in precisely controlling the location and extent of the ablation.

Some of the problems with conventional fluoroscopic positioning of catheters include prolonged radiation exposure, sometimes as long as two hours. Additionally, the clinician may be unable to determine precisely where the catheter is in terms of the endocardium, vessel orifices and cardiac structures, such as valves.

During conventional ablation of cardiac tissue in attempts to destroy arrhythmogenic foci or accessory pathways, pathways causing AV node reentry, and ventricular tachycardia foci, it is difficult to precisely position the ablative function to correspond as closely as possible to the electrical abnormality identified by the mapping procedure. For example, blood flow, cardiac contractions and respiratory motion can alter the position slightly or destabilize the ablative function.

In summary, catheter ablation is applied to patients with worrisome cardiac rhythm disturbances. Current technology involves both (1) the use of mapping catheters to locate areas of cardiac tissue giving rise to electrical abnormalities and (2) the application of radio frequency current to or close to these areas for their destruction. In many situations the abnormal areas are readily found but stabilizing the ablation catheter is difficult because of a peculiar anatomic location or motion of the heart among other factors.

SUMMARY OF THE INVENTION

This invention resides in a method for ablating localized cardiac tissue in a living mammal, the prime example of course being humans, by the use of two catheters with magnetized tips. Collectively, the catheters serve both mapping and ablating functions, permitting both a determination of the locus of an arrhythmia and the ablation of locus to correct the arrhythmia without the need to relocate the locus between these two functions. The magnetic attraction is across cardiac tissue and serves to secure the proper positioning of the ablation function.

While the mapping and ablation functions can be either on a single catheter or divided among the two catheters, the preferred arrangement is the latter, i.e., with one catheter serving as the "targetting catheter" which performs the mapping function, and the other serving as the "ablation catheter" which performs the ablation. In either arrangement, since ablation is done without removal of the targetting catheter, this invention involves a lesser use of such procedures as x-ray exposure and fluoroscopy than conventional methods, as well as a reduction in the risks associated with these procedures. Regardless of the arrangement, both catheters have magnetized tips and are preferably positioned on opposing sides of cardiac tissue.

These and other embodiments of the invention are described in detail below.

BRIEF DESCRIPTION OF THE DRAWINGS

FIGS. 1A and 1B are schematics of the human heart.

FIG. 2A is a schematic of an electrode catheter of the invention.

FIG. 2B is a schematic of a distal tip of an electrode catheter of the invention.

FIG. 2D is a schematic of an alternative anchoring catheter of the invention.

DETAILED DESCRIPTION OF THE INVENTION AND PREFERRED EMBODIMENTS

Figure 1B:
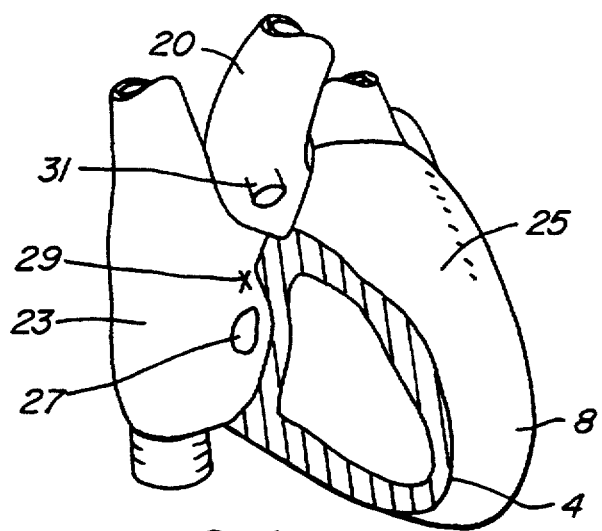

While this invention is sufficiently broad in scope to encompass a variety of arrangements, modalities and procedures, this description will focus on certain specific embodiments as a means of generating an understanding of the invention as a whole. The preferred embodiment in which one catheter is a targetting catheter serving the mapping function, and the other catheter is an ablation catheter, will now be described in detail.

In accordance with this preferred embodiment, the targetting catheter is advanced into the heart and placed in contact with the heart tissue at a multitude of locations in succession. During this process, electrode rings at the tip of the catheter are used to map electrical activation of the heart. The term "contacting" as used herein includes placing the electrode in the vicinity of the locus, preferably in a position to most easily detect the electrical abnormality. Once a region containing an irritable zone or abnormal pathway is detected, the targetting catheter is held in that position and its magnetized region is used to attract the ablation catheter. The ablation catheter is maneuvered to the point where it and the targetting catheter are held in place by the magnetic attraction between their magnetized regions. The ablative function will then be at the identified locus, appropriately positioned and stabilized.

Maneuvering of the two catheters to place their distal ends at the desired locations inside the heart is achieved by conventional techniques known to those skilled in catheter construction and use. For example, the catheters can be positioned by transseptal puncture techniques. The mapping electrode at the tip of the targetting catheter can thus be placed within a chamber proper such as the atria or the ventricles, or alternatively, within a vessel such as the coronary sinus or a coronary artery. Placement within the coronary sinus gives better access to the abnormal electrical activity from the heart chambers.

While the present invention is broadly applicable to the treatment of patients with cardiac electrical disturbances such as accessory pathways, most of these pathways course over the left AV groove. With the targetting catheter positioned in the coronary sinus, the ablation catheter can be inserted retrogradely, for example, via the aortic valve, or transseptally into the left atrium. Alternatively, the targetting catheter can be positioned in the right side of the heart with the tip of the catheter placed into the right coronary artery instead of the coronary sinus.

The various embodiments of the invention include both bipolar and unipolar systems. In bipolar systems, two internal electrodes are used, one on the distal tip of each catheter, with the two electrodes in two distinct chambers separated by cardiac tissue, such as a portion of the heart wall. Ablation is performed by delivering alternating current to both catheter tips. The currents are initially dense and then diverge only to reconverge resulting in a fairly large localized transtissue or transseptal burn.

In unipolar systems, only one of the catheters contains an electrode, and it serves both mapping and ablation functions. To use a system of this type, a reference electrode pad is placed externally on the patient. Once the electrode-bearing catheter is properly positioned at the locus of the disturbance, the second catheter is inserted such that its magnetized tip will attract the magnetized tip of the electrode-bearing catheter and thereby stabilize the position of the electrode. In these systems, the second catheter is used solely for stabilization of the first.

The magnetized regions may contain any material or combination of materials which would create a magnetic attraction between the two regions. Preferably, the two magnetized regions include a natural magnetic material, i.e., a permanent magnet. Examples are rare earth magnets, such as samarium cobalt or neodymium. Neodymium encased in platinum-iridium is particularly preferred, alto gold-plated samarium cobalt (SmCo) is a useful alternative. The gold plating provides biocompatibility and a uniform RF field (i.e., one in which there are few or no hot spots). Even more preferred is sintered SmCo, which permits the addition of small quantities of electrical conductor to improve ablation. For neodymium magnets, neodymium of grade in the range of $(BH)_{max}=25$ to 35 MG•Oe (megaGauss•oerstad) is suitable. Alternative magnetic materials are ferromagnetic materials such as iron, nickel, cobalt and alloys of titanium or aluminum. Further alternatives are electromagnets. The magnets will most conveniently be mounted on the catheters such that their north/south direction will be in alignment with the longitudinal axes of the catheters, with the north pole distal relative to the south pole.

Since the magnetic attraction between the two catheters is through cardiac tissue, the tips of the two catheters are not in physical contact with each other. The intervening tissue can be endocardial, subvalvular or intravascular tissue. Thus, the term "chamber" as used herein includes not only the four chambers proper of the heart, but also intravascular regions in the vicinity of the heart such as the coronary sinus. Intravascular tissue of particular interest in this invention is tissue at the coronary sinus and the tricuspid annulus.

In further preferred embodiments of the invention, a method permitting visualization of the position of the catheter tips is incorporated into the procedure to assist with one or more of the steps. Fluoroscopy is one example of a visualization technique suitable for use in this context; ultrasound is another. Still further examples will be readily apparent to those skilled in the art.

The ablative function may be any of a number of functions capable of destroying tissue or suppressing the electrical activity of tissue. Preferably the ablative function is one which emits radio frequency (RF) energy. Alternative functions are those which emit laser or microwave energy or cold (for cryotherapy). Further alternative functions are those which emit a drag such as lidocaine or a substance such as saline which have a temporary effect on the cardiac tissue and reduce or eliminate the electrical abnormality on a temporary basis. Still further alternatives are the emission of compounds which destroy the identified locus. Ethanol is an example of such a compound. Thus, ablative functions of the present invention include both those that entail permanent tissue destruction as well as those that provide only a temporary effect.

For those embodiments of the invention in which RF is the ablation modality, the optimal dose of RF will vary with the clinical circumstances. Determination of the optimal dose in any particular case is within the ability of one of ordinary skill in the In general, however, best results will be achieved with RF in the range of from about 100 KHz to about 1 MHz, and preferably from about 300 to about 500 Hz. The RF energy is preferably applied at a temperature of from about 45° C. to about 70° C. for a period of time ranging from about 10 to about 120 seconds. A typical dose will be about 300 to 500 KHz applied for about 60 seconds at about 60° C. Expressed in watts, the RF dose will generally range from about 10 to about 60 watts, and preferably from about 25 to about 40.

Turning now to the drawings, the general anatomic structure of the heart is illustrated in FIGS. 1A and 1B. The heart contains four chambers: the right atrium 2, the right ventricle 4, the left atrium 6 and the left ventricle 8. Venous return from the body enters the tight atrium 2 by the superior vena cava 10 and inferior vena cava 12. Additionally, blood from the heart wall drains into the tight atrium 2 through the opening of the coronary sinus 27. The coronary sinus runs in the posterior atrioventricular (AV) groove which is a shallow depression between the atria and ventricles and which is also known as the sulcus coronarius cordis.

Blood which has collected in the right atrium 2 enters the right ventricle 4 after passing through the tricuspid valve 24. The collected oxygen poor blood in the tight ventricle 4 exits the heart through the pulmonary valve 26 and enters the main pulmonary trunk which splits into tight and left pulmonary arteries 14, 16. After oxygenation in the lungs, the blood is returned to the left atrium 6 by the pulmonary veins 18. The blood passes from the left atrium 6 into the left ventricle 8 through the mitral valve 28. The blood exits from the left ventricle through the aortic valve 30 and into the aorta 20 from which it is distributed to the body.

The left and tight ventricles 4, 8 are separated by a wall denoted the ventricular septum or interventricular septum 22. Similarly, the tight and left atria 2, 6 are separated by the atrial septum or interatrial septum 23. Each cardiac valve is supported at its base by a ring structure called an annulus. Thus, placement of a catheter tip at the mitral annulus means placement in the vicinity of the ring-shaped base of the mitral valve.

An illustrative electrode catheter for use in accordance with the invention is shown in FIG. 2A. The electrode catheter includes a catheter assembly 40 which in turn includes several proximal leads 42, a handle 44 including a steering mechanism, and a catheter 46. The proximal leads are attached to an energy source and a recording machine (not shown). The handle 44 includes a steering device which, in turn, typically includes a mechanism having a screw for tension adjustment and a guide wire which extends into the catheter 46. The catheter 46 terminates at its distal end in a tip 48.

An enlargement of the distal tip 48 is shown in FIG. 2B. The distal tip 48 includes an electrode 50, several electrode rings 52, a control wire assembly 54 which is operably connected to the steering device of handle 40, a thermistor (not shown) and a distal tube covering 56. The thermistor is used to determine the temperature at the electrode tip 50 to assist with RF application. Typically, the distal tip 48 includes four, six or eight electrode rings 52 which are used for mapping.

In the distal tip 48, the electrode 50 is formed of a magnetic material as described above. The magnetic materials used in the two catheters should be materials which produce a magnetic attraction effective over a distance of at least about one half inch.

The distal tube cover 56 is preferably formed of a material such as polyurethane. The electrode rings 52 may be formed of any conventional electrode material; platinum is preferred. The outer diameter of the distal tip 40 can be varied as appropriate, and it typically about 6 to 8 French (F) with 7 F preferred.

The catheters of this invention can be similar to standard catheters presently used for cardiac catheterization, modified by the inclusion of a magnet or a magnetized region in the distal tip. For example, a standard catheter can be obtained from EP Technologies, Inc. under the product name of SteeroCath (EPT, Inc., 350 Potrero Avenue, Sunnyvale, Calif. 94086, U.S.A.), and can be adapted for use according to the invention by the incorporation of a magnetized region.

Figure 2C:
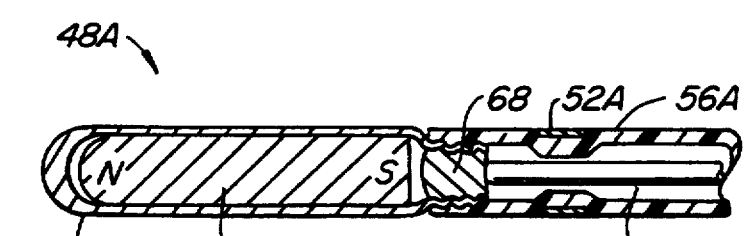
FIG. 2C is a schematic of an alternative distal tip of an electrode catheter of the invention.

An example of an ablation catheter 48A is depicted in FIG. 2C. The catheter contains a control wire assembly 54A, a distal tube covering 56A, and electrode rings 52A equivalent to those of the example in FIG. 2B. The catheter further contains an ablation tip 64 which may for example be formed of a platinum iridium alloy, which, in conjunction with the electrode tings 52A supplies the ablation function. The ablation tip 64 surrounds a permanent magnetic core 66. A soldered joint 68 fastens the tip 64 to the control wire assembly 54A.

A catheter 48B which functions solely as an anchoring catheter, with a magnetic tip but no mapping or ablation functions (i.e., used in procedures involving unipolar ablation), is depicted in FIG. 2D. The catheter body 56B, the control wire assembly 54B and the magnetic core 66B are equivalent to the previously described embodiments. The distal tip covering 60 over the magnetic core 66B is formed of a biocompatible material which does not interfere with the magnetic properties of the core 66. Examples of such biocompatible materials are gold, platinum, platinum alloys and plastics such as polyurethane or teflon. A solder or pressure-fit joint 68B fastens the distal tip to the catheter body 56B by appropriate means such as soldering.

Once the procedure is completed, the patient should be monitored as after any conventional procedure for the treatment of cardiac arrhythmias. Post-procedural monitoring generally includes assessment by inquiry and physical examination, as well as laboratory determination of parameters such as cardiac enzyme levels and electrocardiograms (EKGs).

EXAMPLE 1

Catheterization of the Coronary Sinus—Transseptal Technique

Employing conventional sterile technique and local anesthesia, the tight femoral vein of a patient suffering from a potentially life-threatening tachycardia is catheterized with a catheter containing mapping electrodes and a magnetized region at its distal tip, with the distal tip of the catheter advanced through the right atrium and into the coronary sinus. Fluoroscopic visualization is used to assist with placement of the catheter.

Figure 3:
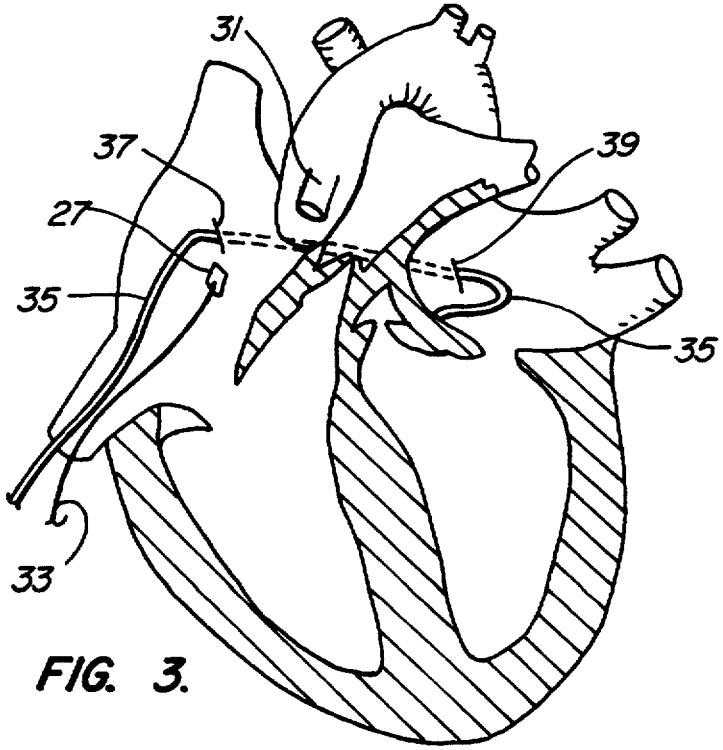
FIG. 3 is a schematic of a method of the invention demonstrating a transseptal technique of coronary sinus catheterization.

After appropriate cardiac mapping to identify the abnormal electrical focus, a second catheter, one which has a magnetized region and an RF ablative function at its distal tip, is inserted through the femoral vein and advanced into the left atrium using a transseptal puncture technique. The second catheter is advanced to the region of the mitral annulus, as shown in FIG. 3. Once the two catheters are positioned and held in place by the mutual magnetic attraction, RF energy is applied at 60° C. for 60 seconds so that the identified focus of the tachycardia is destroyed. The catheters are then withdrawn and the patient is closely monitored. In an alternative arrangement, the first catheter may contain both the mapping electrodes and the RF component, and the second catheter may then serve strictly as an anchoring catheter to secure the position of the first catheter.

EXAMPLE 2

Catheterization of the Coronary Sinus—Retrograde Technique

Figure 4:
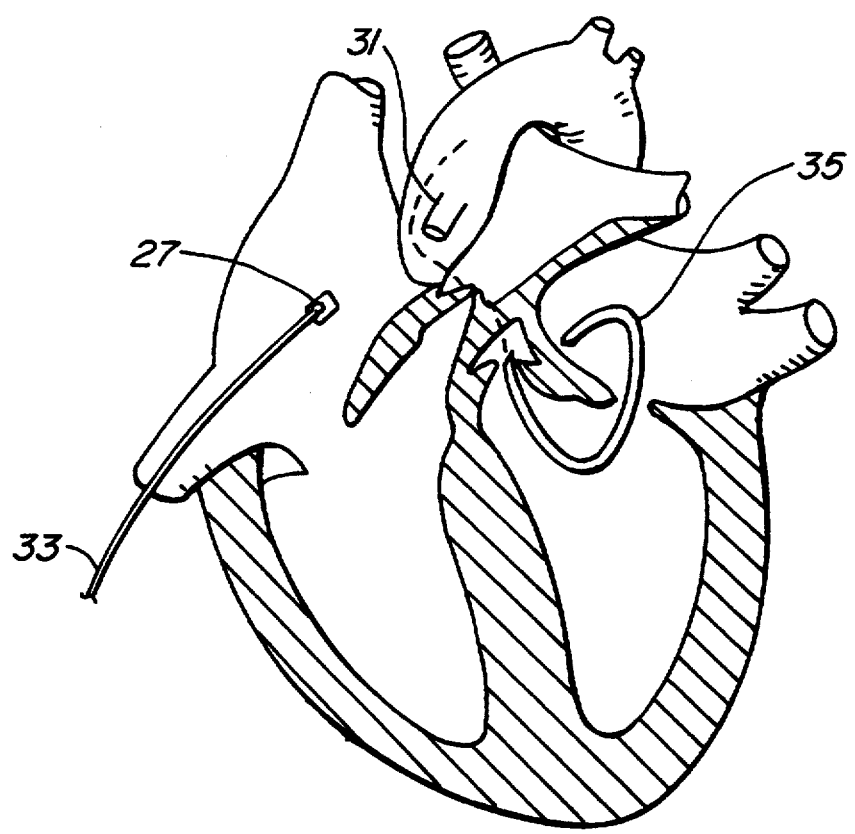
FIG. 4 is a schematic of a method of the invention demonstrating a retrograde technique of coronary sinus catheterization.

The procedure is equivalent to that described in Example 1 except for the following. After mapping, the second catheter is initially inserted into an artery, advanced to the aorta and retrogradely pushed through the aortic valve into the left atrium, as shown in FIG. 4. The catheters are mutually attracted and accordingly stabilized as in Example 1.

The foregoing is offered primarily for purposes of illustration. It will be readily apparent to those skilled in the art that the operating conditions, materials, procedural steps and other parameters of the system described herein may be further modified or substituted in various ways without departing from the spirit and scope of the invention. For instance, the anchoring catheter could be used for ablation, or even mapping, in appropriate circumstances. Thus the invention is not limited by the description and examples, but rather by the appended claims.

What is claimed is:

1. A method for facilitating localized ablation of cardiac tissue which gives rise to an electrical abnormality in the heart of a living mammal, said method comprising:
  (a) inserting a distal end of a first catheter into a first chamber of said heart suspected of containing such an electrical abnormality, said distal end having a mapping electrode and a first magnetically attracting region;
  (b) placing said mapping electrode in contact with tissue at a plurality of positions thereon in succession while monitoring electrical signals generated in said heart until a locus of electrical abnormality in said cardiac tissue is detected;
  (c) inserting a distal end of a second catheter into a second chamber of said heart, said distal end having a second magnetically attracting region magnetically attracted to said first magnetic attracting region, one of said first and second catheters containing a means for ablation at the distal end thereof;
  (d) with said mapping electrode at said locus, maneuvering said distal end of said second catheter to draw said first and second magnetically attracting regions into mutual magnetic attraction through cardiac tissue; and
  (e) activating said means for ablation to reduce said electrical abnormality.

2. A method in accordance with claim 1 wherein the electrical abnormality of step (a) is a supraventricular tachycardia.

3. A method in accordance with claim 1 wherein step (b) includes placing of the mapping electrode in the coronary sinus.

4. A method in accordance with claim 1 wherein step (c) comprises transseptal insertion of the distal end of the second catheter and the second chamber is the left atrium.

5. A method in accordance with claim 1 wherein the reduction of said electrical abnormality of step (e) comprises effecting permanent tissue destruction.

6. A method in accordance with claim 1 further comprising using a means for visualization to assist with at least one of the steps.

7. A method in accordance with claim 1 wherein the living mammal is a human.

8. A method for facilitating localized ablation of a locus of cardiac tissue which gives rise to an abnormal tachycardia in the heart of a human, said method comprising:
  (a) inserting a distal end of a first catheter into a first chamber of said heart suspected of containing such a locus, said distal end containing a mapping electrode and a first natural magnetic substance;
  (b) placing said first electrode in contact with tissue at a plurality of positions thereon in succession while monitoring electrical signals generated in said heart until said locus is detected;
  (c) inserting a distal end of a second catheter into a second chamber of said heart, said distal end having both a means for ablation which includes the capability to emit radio frequency and a second natural magnetic substance attracted to said first natural magnetic substance;
  (d) with said mapping electrode at said locus, maneuvering said second catheter to guide said distal end of said second catheter towards said locus through mutual magnetic attraction between said first and second natural magnetic substances through cardiac tissue; and
  (e) activating said means for ablation to emit radio frequency to reduce said locus.

9. A method in accordance with claim 8 wherein said first chamber of step (a) is the right atrium and step (b) comprises placing the mapping electrode in the coronary sinus.

10. A method in accordance with claim 8 wherein said second chamber of step (c) is the left atrium and step (c) comprises inserting the distal end of said second catheter transseptally.

11. A method in accordance with claim 8 further comprising inserting said second catheter into the right atrium before step (c) and accomplishing step (c) by performing transseptal puncture.

12. A method in accordance with claim 8 wherein step (e) comprises destroying tissue at said locus.

13. A method in accordance with claim 8 wherein at least one of said steps (a) and (c) comprising inserting said catheter into the femoral vein.

* * * * *